United States Patent [19]
Spiro

[11] 4,014,327
[45] Mar. 29, 1977

[54] TENNIS ELBOW SPLINT

[76] Inventor: Irving Spiro, 7925 West Drive, North Bay Village, Fla. 33141

[22] Filed: Apr. 16, 1976

[21] Appl. No.: 677,831

[52] U.S. Cl. .............................. 128/165; 273/189 A
[51] Int. Cl.² .......................................... A61F 13/00
[58] Field of Search ....... 128/87, 89, 165, DIG. 15, 128/77; 273/189 A

[56] References Cited
UNITED STATES PATENTS

| | | | |
|---|---|---|---|
| 1,414,012 | 4/1922 | Flint | 128/87 R X |
| 2,809,042 | 10/1957 | Wasley | 128/189 A X |
| 3,693,973 | 9/1972 | Wattenburg | 273/189 A X |
| 3,877,426 | 4/1975 | Nirschl | 128/165 |

*Primary Examiner*—John D. Yasko
*Attorney, Agent, or Firm*—Salvatore G. Militana

[57] ABSTRACT

A tennis elbow splint having a metal bar encased in an elongated pocket that is fastened at each end to a band, one band adapted to extend about the wrist of the user and a second band adapted to extend about the forearm with the metal bar engaging the palm side of the forearm. Each of the bands being provided with a metal loop at one end and a Velcro fastening strap at the other end whereby the bands rimly engage the wrist and forearm of the user while playing tennis to provide relief to the user having tennis elbow as well as preventing the user from developing tennis elbow.

1 Claim, 5 Drawing Figures

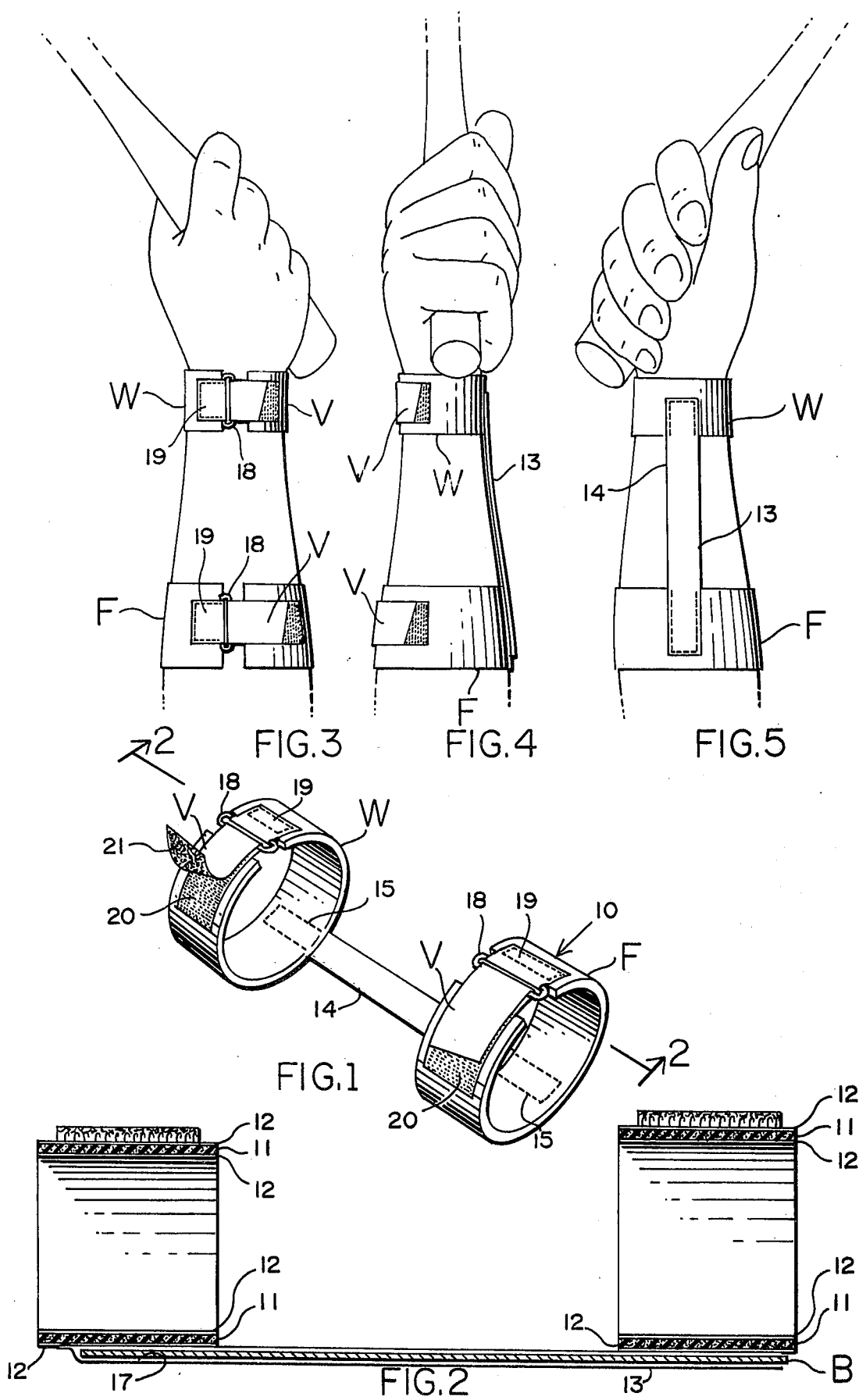

TENNIS ELBOW SPLINT

BACKGROUND OF THE INVENTION

1. Field of the Invention

This invention relates generally to orthopedic splints and is more particularly directed to one for use by tennis players who have tennis elbow or wish to prevent developing this ailment while playing tennis.

2. Description of the Prior Art

At the present time, a person who is afflicted with epicondylitis commonly known as "tennis elbow" treats it by refraining from participating in the sport, and thereby resting the torn muscles concerned and permitting the abating of the inflammation of the ligaments that join the two bones of the forearm, namely the radius and the ulna, to the two spurs or epicondyles on the end of the humerus or upper arm bone. He will take certain medication such as aspirin, injections of cortisone, etc., and hope that in due time he will be able to play tennis again. Those persons having tennis elbow, whose pain may not be severe and who wish to play tennis, will wear a tight elastic band about his forearm below his elbow to decrease the tension on the forearm muscles. This type of device has proved inadequate to prevent and relieve a person with tendonitix, strained tendons, or myositis, (inflamed muscles.) In addition, the elastic band prevents him from being able to stroke the tennis racquet properly and thereby affecting his ability to participate in this sport. The present invention contemplates avoiding the latter objection to the use of a tight elastic band as well as providing the user with relief from tennis elbow while playing if he is afflicted by it in addition to the prevention of acquiring tennis elbow.

BRIEF SUMMARY OF THE INVENTION

The present invention when positioned properly on a person's wrist and forearm provides such support as to strengthen the wrist and forearm muscles of the user who now acquires the ability to provide a firmer grip on the tennis racquet for a more powerful swing without allowing the muscles to twist away from the radial bone. The user of my splint is able to play longer than without it and not be as fatigued or have a tired feeling in his forearm.

Since tennis elbow is apparently caused by the repeated jarring impact of the ball on the racquet as the tennis player swings his arm, my splint which has a metal bar lying along the user's forearm and secured to the bands to prevent the slippage of the bands from their position on the wrist and forearm function to keep the arm muscles secure and contracted thereby preventing the straining, spraining or tearing of muscles.

With these and other objects in view, the invention will be best understood from a consideration of the following detailed description taken in conjunction with the accompanying drawing forming a part of this specification, with the understanding, however, that the invention is not confined to any strict conformity with the showing of the drawing but may be changed or modified so long as such changes or modifications mark no material departure from the salient features of the invention as expressed in the appended claims.

BRIEF DESCRIPTION OF THE SEVERAL VIEWS OF THE DRAWING

In the drawing:

FIG. 1 is a perspective view of a splint for tennis elbow constructed in accordance with my invention.

FIG. 2 is a cross sectional view taken along the line 2—2 of FIG. 1.

FIG. 3 is a top plan view of my splint shown positioned on a person's forearm.

FIGS. 4 and 5 are similar views with the person's arm rotated progressively 90° to the right.

DETAILED DESCRIPTION OF THE PREFERRED EMBODIMENT

Referring to the drawing wherein like numerals are used to designate similar parts throughout the several views, the numeral 10 refers generally to my splint consisting of a pair of bands —W— and —F— joined together by a bar —B— contained in an elongated pocket 17. The bands —W— and —F— are identical in construction, but differ in their sizes. Since both of the bands —F— and —W— must engage each of the forearm and wrist respectively in a snug and firm manner, the forearm band —F— is larger in length and width than that of the wrist band —W—.

Each of the bands —F— and —W— consists of a substantially rectangular portion of pliable and soft material construction such as a sandwich formed by a layer of sheet sponge 11 covered on each side by a layer of leather or plastic material 12. At approximately the mid-portion of each of the bands —F— and —W— there is secured thereto as by stitching 15, the pocket 17 formed by a length of cloth 13 folded along one side and stitched at the other side 14 to form the elongated pocket 17 in which the flat metal bar —B— is positioned. The metal bar —B— which is stiff yet slightly resilient is bent slightly to conform with the varying diameter of the forearm so that the bar —B— lies along and provides a slight pressure against the outer surface of the forearm of the person wearing the splint 10. The bands —F— and —W— are wrapped around and held in position on the forearm and wrist portions of a persons arm by means of a metal loop 18 secured to one end of the bands —F— and —W—. This is accomplished by inserting a relatively short length of cloth 19 through the loop 18, folding the cloth 19 about its center portion on itself and securing the ends of the cloth to the end portion of the bands. The fastening straps —V— which have one end sewn to the free edges of each of the bands —F— and —W— have their other end extend through the loops 18 to fold on itself for engagement of the complementary connecting patches 20 and 21. Though other strap securing means can be used, complementary detachable connections consisting of one of the portions 20 having a plurality of small fiber hooks engageable in a complementary patch consisting of a porous pad of fibrous material 21. An example of such a product is known by the trade-mark Velcro.

When a person is desirous of using my splint 10, he extends his arm in a horizontal position with his palm facing upwardly. The bands —F— and —W— are positioned at the forearm and wrist and the bar —B— extends along the upper surface of the forearm as shown by FIG. 5. Then each of the straps —V— are threaded through the loops 19, folded over and pulled until the bands —F— and —W— engage the wrist and forearm firmly. The fibrous material 21 is made to engage the fiber hooks 20 by pressing one on the other, whereby the bands —F— and —W— will maintain their firm position about the forearm and wrist respectively all during the person's activity while playing tennis.

As noted by the above decription of my splint 10 taken in connection with the drawing, the function of my splint 10 is not only to permit the user who has epicondylitis commonly known as tennis elbow, to relief from its pain while playing tennis, but also to prevent one from acquiring a tennis elbow.

What I claim as new and desire to secure by Letters Patent is:

1. A splint for the prevention of tennis elbow and for the relief from its pain comprising a pair of pliable bands adapted to be positioned about the wrist and forearm of a person, a loop secured at one end of each of said bands, a strap secured to the other end of each of said bands, said straps having interengaging fastening surfaces whereby upon said straps extending through said loops and being folded upon themselves for interengagement, said pliable bands are held firmly in position about said wrist and forearm, an elongated and pliable member forming a pocket extending between said bands and an elongated and substantially slightly resilient member received in said pocket extending along and pressing against said forearm.

* * * * *